United States Patent
Woehr

(10) Patent No.: US 10,004,891 B2
(45) Date of Patent: *Jun. 26, 2018

(54) CATHETER ASSEMBLY

(71) Applicant: B. Braun Melsungen AG, Melsungen (DE)

(72) Inventor: Kevin Woehr, Felsberg (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/042,031

(22) Filed: Feb. 11, 2016

(65) Prior Publication Data

US 2016/0158526 A1    Jun. 9, 2016

Related U.S. Application Data

(63) Continuation of application No. 14/890,419, filed as application No. PCT/EP2014/067573 on Aug. 18, 2014.

(30) Foreign Application Priority Data

Aug. 21, 2013 (GB) .................................. 1314953.9
Aug. 29, 2013 (GB) .................................. 1315401.8
(Continued)

(51) Int. Cl.
*A61M 39/24* (2006.01)
*A61M 25/00* (2006.01)
(Continued)

(52) U.S. Cl.
CPC .............. *A61M 39/24* (2013.01); *A61M 5/36* (2013.01); *A61M 25/0097* (2013.01);
(Continued)

(58) Field of Classification Search
CPC ........ A61M 39/24; A61M 5/36; A61M 39/22; A61M 2039/064; A61M 2039/066;
(Continued)

(56) References Cited

U.S. PATENT DOCUMENTS 4,673,393 A    6/1987  Suzuki et al.
4,758,225 A    7/1988  Cox et al.
(Continued)

FOREIGN PATENT DOCUMENTS

AU    2006203663    2/2008
AU    2006203664    2/2008
(Continued)

OTHER PUBLICATIONS

Examiner's Report on corresponding foreign application (RU Application No. 2015140755) from the Russian Intellectual Property Office dated Mar. 24, 2016.
(Continued)

*Primary Examiner* — Andrew Gilbert
*Assistant Examiner* — Hamza Darb
(74) *Attorney, Agent, or Firm* — Klein, O'Neill & Singh, LLP

(57) ABSTRACT

A catheter assembly including a catheter hub being connectable to a device for the infusion or withdrawal of fluids; a hollow extension tube connected at its distal end to the catheter hub, the extension tube connectable at its proximal end to a device for infusing fluid into the chamber within the catheter hub; a valve assembly disposed within the chamber of the catheter hub having a first valve member and a second valve member preventing the flow of fluid through the chamber to or from the proximal end of the catheter hub. A needle guard assembly is also provided.

40 Claims, 10 Drawing Sheets

(30) Foreign Application Priority Data

Oct. 31, 2013 (CN) .......................... 2013 1 052778
Oct. 31, 2013 (CN) ...................... 2013 2 0679130 U

(51) Int. Cl.
| | | |
|---|---|---|
| *A61M 25/06* | (2006.01) | |
| *A61M 39/22* | (2006.01) | |
| *A61M 5/36* | (2006.01) | |
| *A61M 39/06* | (2006.01) | |

(52) U.S. Cl.
CPC .... *A61M 25/0606* (2013.01); *A61M 25/0618* (2013.01); *A61M 25/0625* (2013.01); *A61M 39/22* (2013.01); *A61M 25/0693* (2013.01); *A61M 2039/062* (2013.01); *A61M 2039/064* (2013.01); *A61M 2039/066* (2013.01); *A61M 2039/242* (2013.01)

(58) Field of Classification Search
CPC ...... A61M 2039/242; A61M 2039/062; A61M 25/0625; A61M 25/0618; A61M 25/0606; A61M 25/0097; A61M 25/0693
See application file for complete search history.

(56) References Cited

U.S. PATENT DOCUMENTS

| | | | |
|---|---|---|---|
| 4,838,855 A | 6/1989 | Lynn | |
| 5,084,023 A | 1/1992 | Lemieux | |
| 5,098,405 A | 3/1992 | Peterson et al. | |
| 5,104,389 A * | 4/1992 | Deem | A61M 39/0606 604/167.02 |
| 5,114,408 A | 5/1992 | Fleischhaker et al. | |
| 5,122,121 A | 6/1992 | Sos et al. | |
| 5,169,393 A | 12/1992 | Moorehead et al. | |
| 5,334,161 A | 8/1994 | Gurmarnik | |
| 5,370,624 A | 12/1994 | Edwards et al. | |
| 5,651,772 A | 7/1997 | Arnett | |
| 5,697,907 A | 12/1997 | Gaba | |
| 5,951,515 A | 9/1999 | Osterlind | |
| 5,954,698 A | 9/1999 | Pike | |
| 6,352,520 B1 | 3/2002 | Miyazaki | |
| 6,506,181 B2 | 1/2003 | Meng et al. | |
| 6,652,486 B2 | 11/2003 | Bialecki et al. | |
| 6,749,588 B1 | 6/2004 | Howell et al. | |
| 7,008,404 B2 | 3/2006 | Nakajima | |
| 7,500,965 B2 | 3/2009 | Menzi et al. | |
| 7,628,775 B2 | 12/2009 | Adams et al. | |
| 7,722,569 B2 | 5/2010 | Söderholm et al. | |
| 7,744,567 B2 | 6/2010 | Glowacki et al. | |
| 8,034,035 B2 | 10/2011 | Weaver et al. | |
| 8,079,987 B2 | 12/2011 | Moorehead et al. | |
| 8,187,230 B2 | 5/2012 | Tanabe et al. | |
| 8,308,691 B2 | 11/2012 | Woehr et al. | |
| 8,377,011 B2 | 2/2013 | Weaver et al. | |
| 8,419,688 B2 | 4/2013 | Woehr et al. | |
| 8,484,574 B2 | 7/2013 | Burroughs et al. | |
| 8,529,523 B2 | 9/2013 | Weaver et al. | |
| 8,540,685 B2 | 9/2013 | Moorehead et al. | |
| 8,591,467 B2 | 11/2013 | Walker et al. | |
| 9,114,231 B2 | 8/2015 | Woehr et al. | |
| 9,155,876 B2 | 10/2015 | Sonderegger et al. | |
| 9,278,180 B2 | 3/2016 | Wong | |
| 2001/0053895 A1 | 12/2001 | Vaillancourt | |
| 2003/0060771 A1* | 3/2003 | Bialecki | A61M 25/0618 604/164.08 |
| 2004/0210194 A1 | 10/2004 | Bonnette et al. | |
| 2005/0049555 A1 | 3/2005 | Moorehead et al. | |
| 2005/0251092 A1 | 11/2005 | Howell et al. | |
| 2006/0015071 A1 | 1/2006 | Fitzgerald | |
| 2007/0093778 A1* | 4/2007 | Cindrich | A61M 5/158 604/500 |
| 2007/0191774 A1 | 8/2007 | Carrez et al. | |
| 2007/0225658 A1 | 9/2007 | Jensen et al. | |
| 2008/0108944 A1 | 5/2008 | Woehr et al. | |
| 2008/0108976 A1 | 5/2008 | Johnson et al. | |
| 2008/0140011 A1 | 6/2008 | Hager et al. | |
| 2008/0312638 A1 | 12/2008 | McNeil | |
| 2009/0157013 A1 | 6/2009 | Wong | |
| 2009/0312718 A1 | 12/2009 | Onuma | |
| 2011/0118612 A1 | 5/2011 | Miller | |
| 2011/0282286 A1 | 11/2011 | Argentine | |
| 2011/0301541 A1 | 12/2011 | White et al. | |
| 2012/0078200 A1 | 3/2012 | Woehr et al. | |
| 2012/0123354 A1* | 5/2012 | Woehr | A61M 25/0606 604/272 |
| 2012/0184910 A1 | 7/2012 | Woehr | |
| 2012/0271235 A1 | 10/2012 | Fuchs et al. | |
| 2012/0277680 A1 | 11/2012 | Woehr et al. | |
| 2013/0030370 A1* | 1/2013 | Walker | A61M 25/0618 604/164.08 |
| 2013/0090609 A1 | 4/2013 | Sonderegger et al. | |

FOREIGN PATENT DOCUMENTS

| | | |
|---|---|---|
| CN | 201005762 Y | 1/2008 |
| CN | 201120010 Y | 9/2008 |
| DE | 202007000173 U1 | 4/2007 |
| DE | 202007006190 | 9/2007 |
| EP | 0268480 | 5/1988 |
| EP | 1292355 B1 | 5/2007 |
| EP | 1820532 A1 | 8/2007 |
| EP | 2204204 | 7/2010 |
| EP | 1240916 B2 | 4/2011 |
| EP | 2319556 | 5/2011 |
| EP | 2617447 | 7/2013 |
| GB | 2343118 | 5/2000 |
| JP | 2001-514943 A | 9/2001 |
| JP | 2003-180833 A | 7/2003 |
| JP | 2005-523777 | 8/2005 |
| JP | 2007-136246 | 6/2007 |
| JP | 2008-068116 | 3/2008 |
| JP | 2009-513267 A | 4/2009 |
| JP | 2009-538188 A | 11/2009 |
| JP | 2011-045543 A | 3/2011 |
| JP | 2011-520553 | 7/2011 |
| JP | 2012-135579 A | 7/2012 |
| JP | 2016-116855 | 6/2016 |
| JP | 2016-526395 | 9/2016 |
| MY | 157956 A | 8/2016 |
| RU | 2225232 | 3/2004 |
| WO | WO 9403232 A1 | 2/1994 |
| WO | WO 96/40359 | 12/1996 |
| WO | WO 9703712 A2 | 2/1997 |
| WO | WO 99/08742 A1 | 2/1999 |
| WO | WO 2004/032995 | 4/2004 |
| WO | WO 2005/042073 | 5/2005 |
| WO | WO 2008/021132 | 2/2008 |
| WO | WO 2008/052791 A1 | 5/2008 |
| WO | WO 2008/064332 | 5/2008 |
| WO | WO 2009/142878 | 11/2009 |
| WO | WO 2010/093791 | 8/2010 |
| WO | WO 2012/009028 | 1/2012 |
| WO | WO 2013/016373 | 1/2013 |
| WO | WO 2013063968 A1 | 5/2013 |
| WO | WO 2014/197656 | 12/2014 |
| WO | WO 2015/024904 | 2/2015 |

OTHER PUBLICATIONS

Combined Search & Examination Report from UK Intellectual Property Office on related UK application (GB1314953.9) dated Mar. 6, 2014.
Examination Report from UK Intellectual Property Office on related UK application (GB1314953.9) dated Apr. 11, 2014.
Notification of Grant from UK Intellectual Property Office on related UK application (GB1314953.9) dated Sep. 16, 2014.
Combined Search & Examination Report from UK Intellectual Property Office on related UK application (GB1315401.8) dated Mar. 10, 2015.

(56) References Cited

OTHER PUBLICATIONS

Notification of Grant from UK Intellectual Property Office on related UK application (GB1315401.8) dated Sep. 22, 2015.
Notification of Grant from UK Intellectual Property Office on related UK application (GB1406042.0) dated Sep. 30, 2014.
Combined Search & Examination Report from UK Intellectual Property Office on related UK application (GB1406042.0) dated Apr. 11, 2014.
International Search Report on corresponding PCT application (PCT/EP2014/067573) from International Searching Authority (EPO) dated Dec. 9, 2014.
Written Opinion on corresponding PCT application (PCT/EP2014/067573) from International Searching Authority (EPO) dated Dec. 9, 2014.
Examiner's Report on corresponding foreign application (RU Application No. 2015140755) from the Russian Patent Office dated Aug. 19, 2016.
Non-Final Office Action on co-pending U.S. Appl. No. 15/042,026 dated Jul. 20, 2016.
Examiner's Report on corresponding foreign application (JP Application No. 2015-563128) from the Japanese Patent Office dated Jul. 19, 2016.
Examiner's Report on corresponding foreign application (JP Application No. 2015-242055) from the Japanese Patent Office dated Jul. 19, 2016.
Examiner's Report on corresponding foreign application (JP Application No. 2016-022156) from the Japanese Patent Office dated Jul. 19, 2016.
Final Office Action on co-pending U.S. Appl. No. 15/042,026 dated Nov. 17, 2016.
Decision of Rejection on corresponding foreign application (JP Application No. 2015-563128) from the Japanese Patent Office dated Apr. 18, 2017.
Office Action on corresponding foreign application (JP Application No. 2015-242055) from the Japanese Patent Office dated Apr. 18, 2017.
Office Action on corresponding foreign application (JP Application No. 2016-022156) from the Japanese Patent Office dated Apr. 18, 2017.
International Preliminary Report on Patentability on corresponding PCT application (PCT/EP2014/067573) from International Searching Authority (EPO) dated Mar. 3, 2016.
Office Action on corresponding foreign application (CN Application No. 201420449512.1) from the State Intellectual Property Office dated Dec. 18, 2014.
Office Action on corresponding foreign application (CN Application No. 201420449512.1) from the State Intellectual Property Office dated Mar. 20, 2015.
Examiner's Report on corresponding foreign application (AU Application No. 2014310651) from the Australian Intellectual Property Office dated Apr. 21, 2016.
Examiner's Report on corresponding foreign application (AU Application No. 2014310651) from the Australian Intellectual Property Office dated Mar. 2, 2017.
Examiner's Report on corresponding foreign application (AU Application No. 2014310651) from the Australian Intellectual Property Office dated Apr. 3, 2017.
Notice of Acceptance on corresponding foreign application (Au Application No. 2014310651) from the Australian Intellectual Property Office dated May 1, 2017.
Office Action on corresponding foreign application (CA Application No. 2,899,744) from the Canadian Intellectual Property Office dated Mar. 15, 2016.
Office Action on corresponding foreign application (CA Application No. 2,899,744) from the Canadian Intellectual Property Office dated Sep. 26, 2016.
Office Action on corresponding foreign application (KR Application No. 10-2015-7022848) from the Korean Intellectual Property Office dated Oct. 26, 2016.
Clear Formalities Report on corresponding foreign application (MY Application No. PI 2015702665) from the Malaysian Intellectual Property Office dated May 17, 2016.
Notification on Patentability Check Results on corresponding foreign application (RU Application No. 2015140755) from the Russian Patent Office dated Apr. 3, 2017.
Supplementary Examination Report on corresponding foreign application (SG Application No. 11201506838X) from the Singaporean Patent Office dated Mar. 3, 2016.
Notice of Eligibility for Grant incl. Supplementary Examination Report on corresponding foreign application (SG Application No. 11201506838X) from the Singaporean Patent Office dated Mar. 24, 2016.
Supplementary Examination Report on corresponding foreign application (SG Application No. 10201509705R) from the Singaporean Patent Office dated Feb. 11, 2016.
Notice of Eligibility for Grant incl. Supplementary Examination Report on corresponding foreign application (SG Application No. 10201509705R) from the Singaporean Patent Office dated Feb. 23, 2016.
Supplementary Examination Report on corresponding foreign application (SG Application No. 10201509708S) from the Singaporean Patent Office dated Jan. 29, 2016.
Notice of Eligibility for Grant incl. Supplementary Examination Report on corresponding foreign application (SG Application No. 10201509708S) from the Singaporean Patent Office dated Mar. 24, 2016.
Non-Final Office Action on co-pending U.S. Appl. No. 15/042,026 dated Jun. 15, 2017.
Examiner's Report on corresponding foreign application (AU Application No. 2016201991) from the Australian Intellectual Property Office dated Apr. 22, 2016.
Examiner's Report on corresponding foreign application (AU Application No. 2016201991) from the Australian Intellectual Property Office dated May 27, 2016.
Examiner's Report on corresponding foreign application (AU Application No. 2016201991) from the Australian Intellectual Property Office dated Mar. 1, 2017.
Notice of Acceptance on corresponding foreign application (AU Application No. 2016201991) from the Australian Intellectual Property Office dated Apr. 7, 2017.
Examiner's Report on corresponding foreign application (AU Application No. 2016201993) from the Australian Intellectual Property Office dated Apr. 27, 2016.
Examiner's Report on corresponding foreign application (AU Application No. 2016201993) from the Australian Intellectual Property Office dated Mar. 3, 2017.
Examiner's Report on corresponding foreign application (AU Application No. 2016201993) from the Australian Intellectual Property Office dated Apr. 4, 2017.
Notice of Acceptance on corresponding foreign application (AU Application No. 2016201993) from the Australian Intellectual Property Office dated May 2, 2017.
Examiner's Report on corresponding foreign application (NZ Application No. 714304) from the New Zealand Patent Office dated Sep. 20, 2017.
Pre-Appeal Reexamination Report on corresponding foreign application (JP Application No. 2015-563128) from the Japan Patent Office dated Oct. 31, 2017.
Decision of Rejection on corresponding foreign application (JP Application No. 2016-022156) from the Japan Patent Office dated Jan. 23, 2018.
Decision of Rejection on corresponding foreign application (JP Application No. 2015-242055) from the Japan Patent Office dated Jan. 23, 2018.
Office Action on corresponding foreign application (KR Application No. 10-2015-7022848) from the Korean Intellectual Property Office dated Sep. 27, 2017.
Non-Final Office Action on co-pending U.S. Appl. No. (U.S. Appl. No. 14/890,419) dated Jul. 8, 2016.
Final Office Action on co-pending U.S. Appl. No. (U.S. Appl. No. 14/890,419) dated Oct. 18, 2016.

(56) References Cited

OTHER PUBLICATIONS

Non-Final Office Action on co-pending U.S. Appl. No. (U.S. Appl. No. 14/890,419) dated Oct. 5, 2017.
Notice of Opposition to Grant of Patent on related NZ application (NZ Appl. No. 714304) to New Zealand Intellectual Property Office (IPONZ) dated Mar. 26, 2018, 2 pages.
Statement of Case on related NZ application (NZ Appl. No. 714304) to New Zealand Intellectual Property Office (IPONZ) dated Mar. 26, 2018, 16 pages.
Proceeding Correspondence on related NZ application (NZ Appl. No. 714304) from New Zealand Intellectual Property Office (IPONZ) dated Mar. 27, 2018, 2 pages.
Notice of Allowance on co-pending U.S. Appl. No. (U.S. Appl. No. 15/042,026) dated Feb. 20, 2018.
Examination Report No. 1 on corresponding foreign application (AU Application No. 2017203702) from the IP Australia dated Mar. 23, 2018.
Examination Report No. 1 on corresponding foreign application (AU Application No. 2017203707) from the IP Australia dated Mar. 23, 2018.
Examination Report No. 1 on corresponding foreign application (AU Application No. 2017203710) from the IP Australia dated Mar. 23, 2018.

* cited by examiner

CATHETER ASSEMBLY

CROSS-REFERENCE TO RELATED APPLICATION

This is a continuation of co-pending application Ser. No. 14/890,419, filed Nov. 10, 2015, which is a national stage application of International Application No. PCT/EP2014/067573, filed Aug. 18, 2014, which claims priority to GB 1314953.9, filed Aug. 21, 2013, GB 1315401.8, filed Aug. 29, 2013, CN 201310527778.3, filed Oct. 31, 2013, and CN 201320679130.3, filed Oct. 31, 2013, the contents of which are expressly incorporated herein by reference.

FIELD OF ART

The present invention relates to a catheter assembly, in particular to an intravenous catheter assembly.

BACKGROUND OF THE INVENTION

Intravenous (IV) catheters are used to access a vein of a patient, in particular for the provision of fluids to the patient or the removal of fluid, especially blood, therefrom. The IV catheter can be primed with a sterile solution to remove air from the device prior to puncturing the patient. This reduces the risks of the patient developing an air embolism.

An IV catheter assembly comprises a catheter extending from the distal end of a catheter hub. A needle extends through the catheter hub and the catheter, such that the sharpened tip of the needle extends beyond the distal end of the catheter. A typical procedure for insertion of the catheter into the vein of the patient requires the healthcare worker to insert the sharpened needle tip and catheter into the patient to locate the vein. Once the needle tip is located in the vein, the healthcare worker manually forwards the catheter into the vein by sliding the catheter along the shaft of the needle in the distal direction. Once the catheter is properly located in the vein, the needle is withdrawn. The catheter is then secured by taping the catheter hub to the skin of the patient. The vein may then be accessed for the infusion or removal of fluids through the catheter hub and the catheter.

To control the flow of fluids through the catheter and the catheter hub, in particular to prevent blood leaving the vein through the catheter, it is known to provide a valve in the catheter hub.

A device for the drainage or infusion of liquids from or to a patient is disclosed in EP 0 268 480. In one embodiment, the device comprises a catheter hub having a catheter extending therefrom. The catheter hub is provided with a flexible valve therein for controlling the flow of fluid through the catheter hub. A valve opener is provided to open the valve, when fluid is to be infused or withdrawn through the proximal end of the catheter hub. EP 0 268 480 discloses providing the catheter hub with a port extending laterally therefrom. A flexible cylindrical seal extends circumferentially around the inside the catheter hub in line with the port.

U.S. Pat. No. 5,098,405 concerns a side ported catheter adapter with a one piece integral combination valve. The valve is disposed within a hub of the adapter so as to close the bore of the adapter and the side port. The valve assembly comprises a generally cylindrical body extending circumferentially around the interior of the hub in line with the port. The valve assembly further comprises a conical valve element, permitting the flow of fluid into the catheter from the proximal end of the hub. The device of U.S. Pat. No. 5,098,405 does not permit fluids to be removed from the patient and only allows fluids to be infused to the patient through either the proximal end of the adapter hub or the port.

A medical connector is described and shown in WO 96/40359. The connector comprises a body having a primary conduit therethrough and a port. A generally cylindrical valve is located within the body in line with the port. A tab extends from the valve into the port. The valve is normally open, permitting the flow of fluid along the primary conduit. Depression of the tab in the port closes the valve across the primary conduit, preventing the flow of fluid therealong and allowing fluid to be infused to or withdrawn from the connector through the port.

Of more relevance, a catheter apparatus with infusion port and valves is disclosed in WO 2008/052791. The apparatus comprises a hollow catheter extension, the distal end of which can be connected to a catheter. A connecting device is provided on the proximal end of the extension. A port extend radially from the extension and opens into the bore of the extension. A valve assembly is disposed within the extension in line with the port and comprises a first, generally cylindrical valve element closing the port. A second valve element prevents the escape of blood from the extension through the bore in the proximal direction. The second valve element is formed as a two-way valve, so as to permit the flow of fluids in either the distal or the proximal direction.

More recently, WO 2008/052790 discloses a catheter assembly and components thereof. The assembly comprises a valve disposed in the catheter hub and a valve opener. The valve opener is configured to be pushed by an IV set luer connector to open the valve, to allow fluids to be passed through the catheter. A tip protector, operable to cover the tip of the needle as the needle is withdrawn from the catheter through the catheter hub, may be provided within the valve opener.

WO 2012/009028 discloses a flushable catheter assembly. The assembly comprises a catheter adapter having a septum disposed therein. A septum activator is provided to selectively open the septum and allow fluid to flow through the catheter adapter when a coupler is attached to the proximal end of the catheter adapter.

A catheter assembly is disclosed in DE 202007006190 U1.

WO 2004/032995 discloses a method of delivering a local anesthesia and a catheter and needle assembly for use in the same.

A safety shield for a needle is disclosed in WO 2005/042073.

A safety catheter comprising a needle point lock is described and shown in U.S. Pat. No. 5,697,907.

Needle protector devices and assemblies are described in GB 2,343,118.

More recently, WO 2013/016373 discloses a vascular access assembly and a safety device to protect a clinician from accidental needle stick injuries.

There is a need for an improved catheter assembly, in particular one that provides for increased control of the infusion and withdrawal of fluids to and from the patient through the catheter.

SUMMARY OF THE INVENTION

According to the present invention, there is provided a catheter assembly comprising:

a catheter hub having a chamber therein, the catheter hub having a distal end and a proximal end, the catheter hub being connectable at its proximal end to a device for the infusion or withdrawal of fluids to or from the chamber within the catheter hub;

a hollow tubular catheter having a proximal end and a distal end, the catheter being connected at its proximal end to the distal end of the catheter hub, the interior of the catheter opening into the chamber within the catheter hub;

a needle having a sharpened needle tip, in a ready position the needle extending through the chamber in the catheter hub and the catheter with the needle tip extending beyond the distal end of the catheter;

a hollow extension tube having a distal end and a proximal end, the extension tube being connected at its distal end to the catheter hub between the proximal and distal ends thereof, the extension tube opening at its distal end into the chamber within the catheter hub, the extension tube connectable at its proximal end to a device for infusing fluid into the chamber within the catheter hub;

a valve assembly disposed within the chamber of the catheter hub, the valve assembly comprising:

a first valve member closing the distal end of the extension tube and openable under the action of a pressurised fluid within the extension tube; and a second valve member preventing the flow of fluid through the chamber to or from the proximal end of the catheter hub, the second valve member being a two-way valve and openable to permit the flow of fluid through the chamber in the catheter hub in both a proximal and a distal direction.

The device of the present invention comprises a catheter hub. The catheter hub is hollow and has an internal chamber therein, the internal chamber being open at both the proximal and distal ends of the catheter hub. The catheter hub may be formed as a single piece. Alternatively, the catheter hub may be formed as two or more separate pieces connected together.

The catheter hub is formed at its proximal end to be connectable to a device for infusing fluid into the patient or removing fluid from the patient, such as a syringe. Such devices are known in the art and will be familiar to the person skilled in the art. In particular, the inner wall of the proximal end of the catheter hub defining the chamber is provided with an internal Luer taper, that is a female Luer taper, allowing standard fittings having a standard male Luer taper to be connected to the proximal end of the catheter hub. The person skilled in the art will be familiar with the Luer taper standard and its requirements.

In one embodiment, the catheter hub comprises a distal hub portion and a proximal hub portion. The proximal hub portion is as hereinbefore described and is connectable to a device for infusing fluid into or removing fluid from the patient. The distal hub portion may have any suitable form. In one embodiment, the distal hub portion has a generally flattened form, such that the catheter hub lies flatter against the skin of the patient and protrudes less from the patient's skin in use. More preferably the distal hub portion comprises wing members extending from opposing sides of the distal hub portion. The wing members increase the stability of the catheter assembly, in particular when the catheter has been inserted into the vein of the patient, and may be used to secure the catheter hub to the skin of a patient, for example by way of adhesive tape. In this way, movement of the catheter hub and the catheter is restricted, in turn reducing the occurrence of phlebitis of the vein of the patient.

A hollow tubular catheter is connected to the catheter hub and extends from the distal end of the catheter hub.

The catheter assembly further comprises a needle having a sharpened needle tip and a bore therethrough. In a ready position, the needle is connected at its proximal end to a needle hub, as is known in the art, and extends through the catheter hub and the catheter in a ready position. In the ready position, the sharpened needle tip is distal of the distal end of the catheter, allowing the needle and the catheter to be introduced into a vein of the patient, in known manner. The needle hub preferably has a chamber therein in communication with the bore in the shaft of the needle, whereby blood flashback in the needle hub chamber may be observed by the user to indicate proper placement of the needle in the vein, in a known manner. The needle hub chamber is typically plugged at its proximal end with a vented plug that allows air to vent from the chamber, but not blood to flow through the plug.

As the needle tip is withdrawn into the hollow tubular catheter a secondary blood flashback occurs between the outside of the needle and the inside of the catheter.

A condition for both the primary and secondary blood flashback is that the air in the catheter device can be displaced by the blood as the air is vented out of the proximal end of the device.

In one embodiment, the needle is provided with an opening, such as a slot, in the shaft of the needle in the distal end portion of the needle and spaced from the sharpened needle tip. In the ready position, the slot is disposed within the tubular catheter. In use, once the needle tip has been inserted into the vein, blood may flow along the bore in the needle, through the slot and into the catheter around the needle shaft. The blood can then flow from the catheter into the catheter hub, to provide a flashback to the user.

The catheter assembly of the present invention further comprises a hollow extension tube having a distal end and a proximal end. The extension tube is flexible. The extension tube is connected at its distal end to the catheter hub between the proximal and distal ends thereof. Preferably, the distal end of the extension tube is connected to the distal portion of the catheter hub. The extension tube opens at its distal end into the chamber within the catheter hub, to allow fluid to flow between the extension tube and the internal chamber. The extension tube is connectable at its proximal end to a device, such as a syringe, for infusing fluid into the chamber within the catheter hub. For example, the extension tube may be provided at its proximal end with a connection hub, preferably a hub having a female Luer taper.

In use, fluid may be introduced into the catheter hub and the catheter by way of the extension tube. By having the device for introducing fluid connected at the proximal end of the extension tube, it may be located away from the catheter hub and the catheter located in the vein of the patient. By having the extension tube flexible, movement of the catheter hub and the catheter as a result of the action of connecting or disconnecting the fluid delivery device at the proximal end of the extension tube is reduced or eliminated. This in turn reduces the occurrence of phlebitis of the vein in the region of the catheter.

The catheter assembly comprises a valve assembly disposed within the internal chamber of the catheter hub. The valve assembly, when closed, prevents the flow of fluid between the extension tube and the internal chamber of the catheter hub and the flow of fluid in either the proximal or distal direction through the internal chamber. The valve assembly comprises a first valve member, which may be opened to permit fluid to flow from the extension tube into the internal chamber of the catheter hub. In this respect, the valve assembly may be a one-way valve between the extension tube and the internal chamber of the catheter hub. The valve assembly comprises a second valve member, which may also be opened to permit fluid to be supplied from the proximal end of the catheter hub in the distal direction to the catheter or to allow fluid to be withdrawn in the proximal direction from the catheter to the proximal end of the catheter hub. In this way, the valve assembly is operable as a two-way valve to control fluid flow through the catheter hub to and from its proximal end.

The first valve member controls the flow of fluid between the extension tube and the internal chamber of the catheter hub. In a preferred embodiment, the first valve member comprises a flexible, resilient valve body. Under the action of increased fluid pressure in the extension tube, the valve body yields, opening the distal end of the extension tube and permitting fluid to enter the catheter hub. The valve body is preferably a tubular body, in particular disposed within the internal chamber of the catheter hub in contact with the inner surface of the wall of the catheter hub. The valve body and the portion of the internal chamber of the catheter hub in which it is disposed may be cylindrical or, in one embodiment, elliptical, in cross-section.

The first valve member may comprise one or more slits therein, aligned with the distal opening of the extension tube and for the passage of fluid therethrough. If the first valve member has one or more slits therein, then it can act as a two way valve and blood or other bodily fluids can be removed through the slits and extension line into a suitable device, such as a syringe or a vacuum collection tube.

The valve assembly comprises a second valve member. As noted above, the second valve member controls the flow of fluid through the internal chamber of the catheter hub to and from the proximal end thereof. The second valve member is disposed in the internal chamber of the catheter hub in a position proximal to the distal opening of the extension tube and the first valve member. In one embodiment, the second valve member comprises a flexible, resilient valve disc extending laterally across the internal chamber of the catheter hub. The disc is provided with one or more closable openings, such as slits, therein, in particular one or more radially extending slits.

The valve assembly may be retained within the internal chamber of the catheter hub by any suitable means. In one embodiment, the valve assembly is retained by friction between the valve members and the inner surface of the catheter hub. Alternatively, the valve assembly may engage with one or more recesses or protrusions formed in the inner surface of the catheter hub.

In the ready position, the needle shaft extends through the valve assembly. The second valve member preferably seals around the shaft of the needle in the ready position, more preferably in a manner that allows gas to vent through the second valve member in the proximal direction, but prevents blood from passing the second valve member. In embodiments in which the second valve member comprises a disc having one or more slits therein, this can be achieved by appropriate arrangement of the or each slit, such that, in the ready position, the or each slit is held open by the needle shaft a sufficient amount to allow the passage of gas but prevent the passage of blood therethrough.

The second valve member may open under the action of a difference in fluid pressure across the valve member. In particular, the second valve member may open under the action of an increased fluid pressure on the proximal side of the valve, to allow fluid to be infused into the catheter and vein of the patient. Similarly, the second valve member may open under the action of a reduced pressure on the proximal side of the valve, to allow fluid to be withdrawn from the catheter and the vein.

In one embodiment, the catheter assembly further comprises a valve opener disposed within the chamber in the catheter hub. The valve opener is disposed within the internal chamber of the catheter hub proximally of the valve assembly. The valve opener is moveable between a closed position, in which the second valve member is closed, and an open position in which the second valve member is open. The valve opener is moved in the distal direction to the open position by the insertion of a device into the proximal end of the catheter hub, such as a syringe or other male fitting. The valve opener is urged into the closed position by the action of the second valve member closing, for example by the resilience of the valve disc. The valve opener preferably has a passage extending longitudinally therethrough and/or around for the passage of fluid.

Movement of the valve opener in the distal direction is limited by the valve assembly. Preferably, means are provided to limit the movement of the valve opener in the proximal direction. In one embodiment, the inner surface of the catheter hub is provided with one or more protrusions to engage with the valve opener.

In the ready position, the needle shaft extends through the valve opener. One preferred form of valve opener comprises a stem, having a passage therethrough, and a head portion at the distal end of the stem, having a passage therethrough. In use, a device inserted into the proximal end of the catheter hub contacts the stem of the valve opener, urging the valve opener from the closed position into the open position. As the valve opener is moved distally into the open position, the head portion is urged into contact with the second valve member, opening the valve assembly.

The stem may comprise a tube, with the needle extending through the tube in the ready position. Alternatively, the stem may comprise one or more legs extending proximally from the head portion. In one embodiment the region of the head portion contacting the second valve member is generally domed or frusto-conical.

In a preferred embodiment, the catheter device of the present invention is a safety device and comprises a needle guard assembly. The needle guard assembly acts to cover and block the sharpened needle tip as the needle is withdrawn from the catheter in the proximal direction and moved from the ready position into a protected position. In this way, the risk of a needle stick injury occurring is reduced or avoided.

The needle guard assembly may be disposed wholly or partly within the internal chamber in the catheter hub. In particular, the needle guard may be disposed within the catheter hub, such that the needle is in its protected position with the sharpened needle tip blocked by the needle guard assembly while the needle tip is within the catheter hub. Examples of preferred needle guard assemblies for use in such embodiments are disclosed in WO 99/08742. The needle guards of WO 99/08742 are of a passive type, that is the needle tip is blocked by the needle guard as the needle is withdrawn from the ready position into the protected position, without the user having to take any additional actions over and above those required with the use of standard or non-safety devices. Passive needle guards of this type are preferred.

Alternatively, the needle guard assembly may be disposed outside the catheter hub, in particular proximal of the catheter hub. In one preferred embodiment, the needle guard assembly comprises a needle guard housing having a needle guard chamber therein. A needle guard is preferably disposed in the chamber. The needle guard housing may have a portion extending into the proximal end of the catheter hub. For example, the needle guard housing may have a distal end portion comprising a male taper, such as a standard Luer taper, for engaging with a female taper in the proximal end portion of the catheter hub. Alternatively, the needle guard housing may reside completely outside the catheter hub.

The needle guard assembly is preferably releasably engaged with the catheter hub. In one preferred embodiment, the needle guard assembly is engaged with the catheter hub with the needle in the ready position. Movement of the needle to the protected position, in which the needle tip is blocked, releases the needle guard assembly from the catheter hub.

Most preferably, in the protected position, the needle tip is disposed within the needle guard housing and the needle tip is blocked within the housing by the needle guard.

A needle guard is disposed within the needle guard housing. The needle guards of WO 99/08742 may be employed within the needle guard housing.

One particularly preferred form of needle guard for use in the catheter assembly as hereinbefore described comprises at least one arm, the arm being moveable from the ready position into a blocking position in which the sharpened needle tip is blocked. The at least one arm preferably has a distal end portion for extending in front of and blocking the needle tip in the blocking position. The at least one arm may extend parallel to the needle in the ready position or, alternatively may cross the shaft of the needle in the ready position.

In a preferred embodiment, the needle guard comprises a first arm and a second arm. One or, preferably both, of the first and second arms may comprise a distal end portion for blocking the needle tip. The first and second arms may extend along opposing sides of the needle shaft in the ready position. Alternatively, the first and second arms may intersect and cross the needle shaft in the ready position. As noted above, at least one of the first and second arms is provided with a distal end portion for blocking the needle tip in the protected position. In embodiments in which both the first and second arms have a distal end portion, it is preferred that the distal end portions are offset with respect to one another. In this way, the distal end portions may engage over the needle tip.

The first and second arms may be of the same length or of different lengths. Preferably, the first and second arms are of different lengths, especially when both arms are provided with a distal end portion. If a single distal end portion is present, it is preferably disposed on the longer of the first and second arms.

At least one of the distal end portions is provided with an endmost portion that is curved inwards at its free edge. In this way, it is ensured that the needle tip is covered, even if an attempt is made to push the needle guard in the proximal direction, that is back from the protected position, along the needle shaft. The inwardly curved endmost portion acts to hook onto the needle tip, so as to prevent movement of the needle guard in the proximal direction and to prevent the needle tip becoming exposed.

The needle guard comprising one or more arms may be in the form of a resilient or spring clip needle guard.

In a preferred embodiment, the needle guard within the housing comprises a needle trap moveable between a ready position, in which the needle trap is held to one side of the shaft of the needle extending through the housing, and a protected position, in which the needle trap extends across the needle tip and blocks the sharpened needle tip of the needle within the housing. The needle guard further comprises a resilient arm biasing the needle trap into the protected position. The resilient arm bears against the inner wall of the housing to urge the needle trap into the protected position. In addition, the needle guard comprises a coupling arm moveable by the needle trap. In the ready position the coupling arm couples the housing to the proximal end of the catheter hub. Movement of the needle trap from the ready position to the protected position moves the coupling arm to release the housing from the catheter hub.

Accordingly, in a further aspect, the present invention provides a needle guard assembly for a catheter assembly, the needle guard assembly comprising:

a housing for receiving a needle extending therethrough and having a distal end and a proximal end, the housing being connectable at its distal end to the proximal end of a catheter hub;

a needle guard disposed within the housing, the needle guard comprising:

a needle trap moveable between a ready position, in which the needle trap is held to one side of the shaft of the needle extending through the housing; and a protected position, in which the needle trap blocks the sharpened needle tip of the needle within the housing;

a resilient arm biasing the needle trap into the protected position, the resilient arm bearing against the inner wall of the housing to urge the needle trap into the protected position;

a coupling arm, in the ready position the coupling arm coupling the housing to the proximal end of the catheter hub, movement of the needle trap from the ready position to the protected position moving the coupling arm to release the housing from the catheter hub.

The needle trap may be connected at one end to the resilient arm. In a preferred embodiment, the needle trap is pivotally attached at a first end thereof to the resilient arm. The resilience of the resilient arm may be provided partly or wholly by resilience in the pivotal connection between the needle trap and the resilient arm. In one embodiment, the needle trap and the resilient arm are folded together on one side of the needle shaft when in the ready position, such that the needle trap overlies the resilient arm.

In the protected position, the needle trap extends distally across the sharpened needle tip, thereby blocking the needle tip and preventing a needle stick injury. The needle trap may comprise one or more lateral members extending in the proximal direction from each side of the needle trap. The lateral members act to retain the needle trap in position relative to the sharpened needle tip, in particular preventing the needle tip from emerging to one side of the needle trap. In use, the needle trap transitions between the ready position, across the needle tip and into the protected position. Further, the needle trap may comprise a retaining member preventing the needle trap from moving in the reverse direction, that is towards its ready position, relative to the needle.

The needle guard further comprises a coupling arm. In the ready position, the coupling arm engages with the catheter hub, to hold the needle guard assembly on the proximal end of the catheter hub. In a preferred embodiment, the coupling arm engages with the outside of the catheter hub, for example with a flange on the proximal end of the catheter hub. The coupling arm is moved by the needle trap transitioning from the ready position to the protected position out of engagement with the catheter hub, thereby releasing the needle guard assembly from the catheter hub. In this way, the needle guard assembly is only released from engagement with the catheter hub once the sharpened needle tip is blocked within the needle guard housing. The coupling arm is preferably connected to the needle trap. In one preferred embodiment, the coupling arm is connected to an end of the needle trap, in particular to a second end of the needle trap opposite the first end. The connection between the coupling arm and the needle trap is preferably pivotal and may be a resilient pivotal connection.

In one preferred embodiment, the resilient arm, the needle trap and the coupling arm are formed as a single component, with resilient pivotal connections between the resilient arm and the needle trap and between the needle trap and the coupling arm, the resilient connections biasing the needle trap into the protected position and the coupling arm out of engagement with the catheter hub.

The position of the needle trap is preferably stabilised both by the coupling arm engaging with the wall of the needle guard housing on one side of the needle shaft and by the resilient arm engaging the wall of the needle guard housing on the opposite side of the needle shaft. In one preferred embodiment, the coupling arm extends through an opening in the wall of the needle guard housing.

In one embodiment, the coupling arm extends around the needle shaft in the ready position, preferably within the needle guard housing. In a preferred embodiment, the coupling arm comprises an opening, the needle shaft extending through the opening in the coupling arm in the ready position.

In the protected position, the needle trap extends distally across the sharpened needle tip and prevents the needle moving in the distal direction relative to the needle guard assembly. The needle guard assembly further comprises means for limiting movement of the needle in the proximal direction relative to the needle guard assembly, so as to prevent the needle guard assembly from leaving the distal end of the needle. The limiting means may comprise a tether, for example extending between the needle hub and the needle guard housing. Preferably, the needle comprises a bulge, such as a crimp, in the distal end portion of the needle shaft spaced from the needle tip. The needle guard assembly, preferably the needle guard housing, comprises a proximal wall having an opening therein, the needle shaft extending through the opening in the proximal wall. The bulge in the needle shaft has a radial dimension that is larger than that of the opening in the proximal wall, such that the bulge and the distal end of the needle cannot pass through the opening. The region of the proximal wall surrounding the opening may be reinforced, for example by way of a metal ring or washer, to prevent the bulge in the needle shaft being inadvertently pulled through the proximal wall of the housing. This is particularly advantageous when the needle guard housing is formed from a relatively soft material, such as plastic. In the ready position, the bulge in the needle shaft preferably lies within the hollow catheter. When the bulge is non-circular it has the advantage of allowing blood to flow between the inside of the catheter and the outside of the needle, to provide the secondary blood flashback.

In a further aspect, the present invention provides an IV catheter assembly comprising a needle guard assembly as hereinbefore described.

BRIEF DESCRIPTION OF THE DRAWINGS

Embodiments of the present invention will be described, by way of example only, having reference to the accompanying drawings, in which:

FIG. 7a is a cross-sectional view of a valve assembly for use in the devices of any of FIGS. 1 to 6;

FIG. 7b is a proximal end view of one embodiment of the valve assembly of FIG. 7a;

FIG. 7c is a proximal end of a second embodiment of the valve assembly of FIG. 7a.

DETAILED DESCRIPTION

Figure 1:
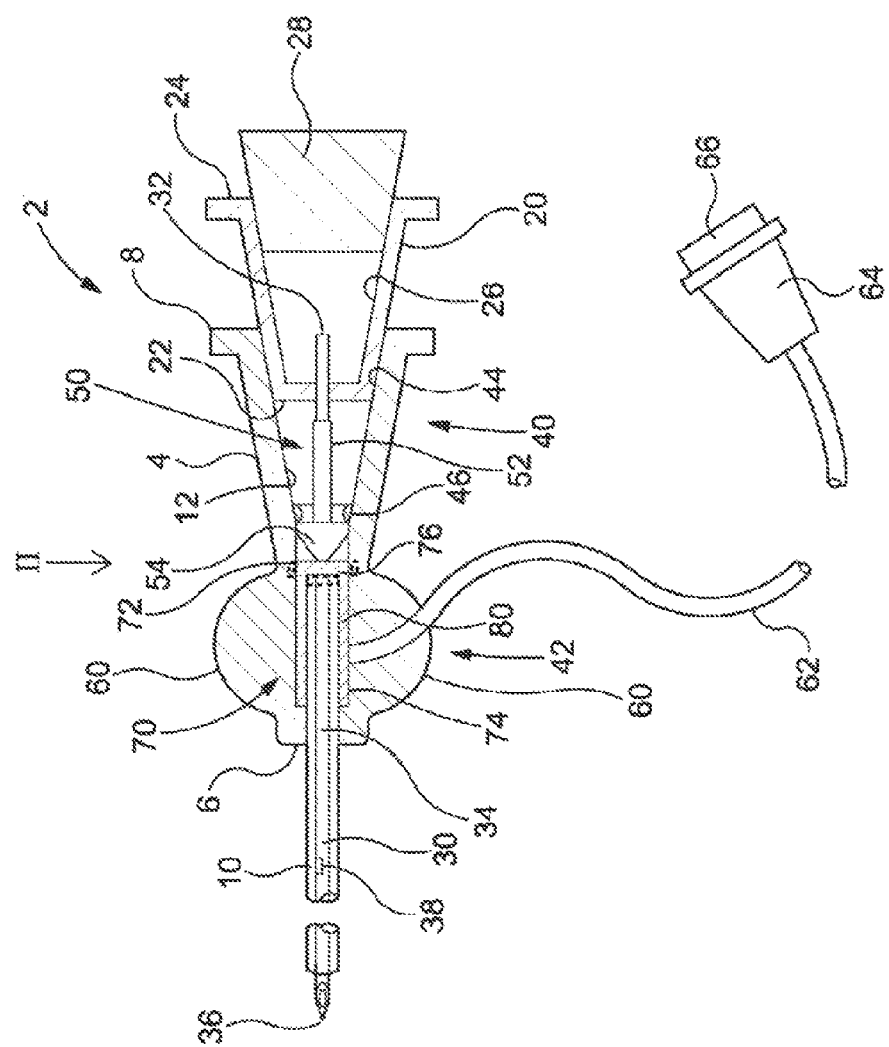
FIG. 1 is a cross-sectional view of a device according to a first embodiment of the present invention in a ready position.
Figure 2:
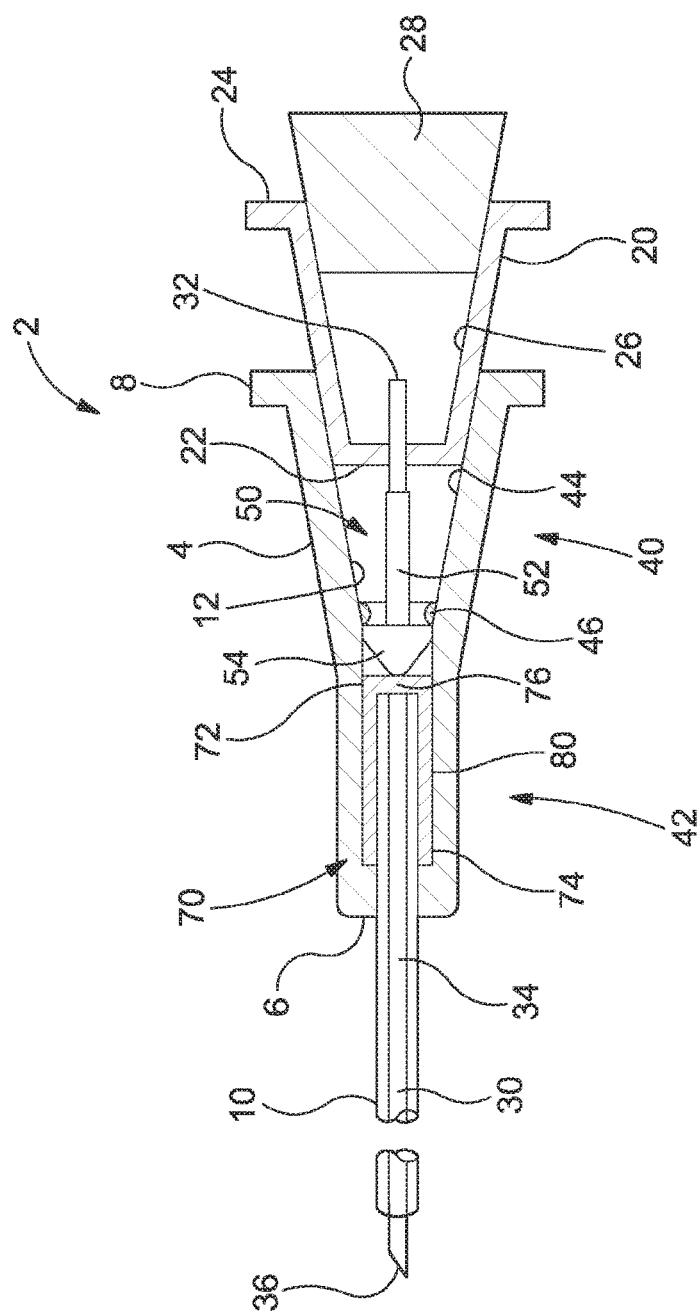
FIG. 2 is a cross-sectional view of the device of FIG. 1 in the direction II.
Figure 3:
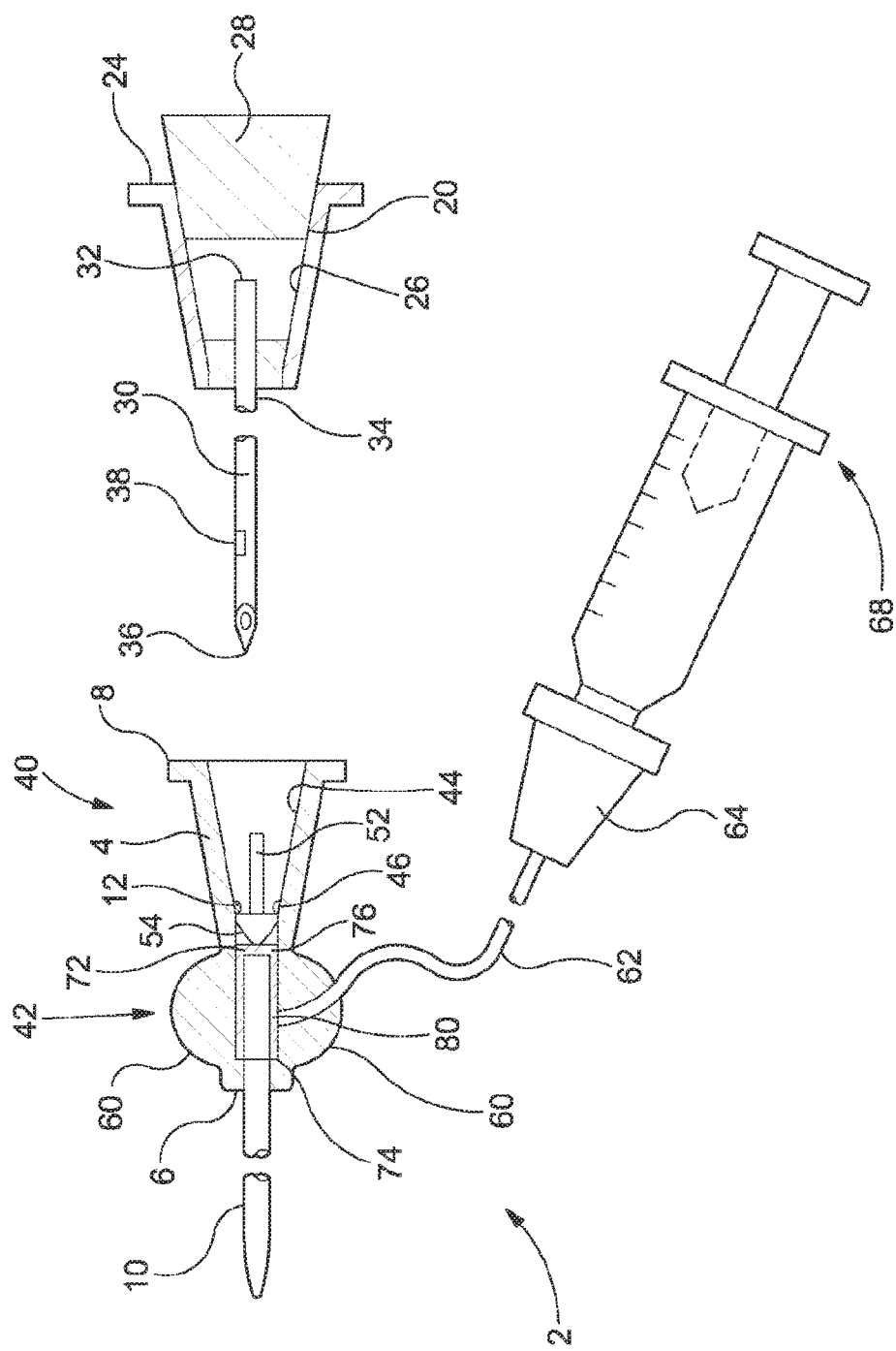
FIG. 3 is a cross-sectional view of the device of FIG. 1 in a retracted position.

Referring to FIGS. 1 and 2, there is shown a device according to a first embodiment of the present invention, generally indicated as 2. The device 2 is shown in FIGS. 1 and 2 in a ready position. The device is shown in FIG. 3 in a retracted position, that is with the needle withdrawn in the proximal direction.

The device 2 comprises a catheter hub 4 having a distal end 6 and a proximal end 8. An elongate, hollow, tubular catheter 10 is connected to the catheter hub 4 and extends from the distal end 6 of the catheter hub, in known manner. The catheter hub 4 comprises an internal chamber 12. The internal chamber 12 is open at the proximal end 8 of the catheter hub 4 and communicates with the hollow catheter 10 at the distal end of the catheter hub. Details of the catheter hub are described in more detail below.

A generally cylindrical needle hub 20 has a distal end 22 and a proximal end 24. The needle hub 20 is formed with an internal chamber 26, the open proximal end of which is closed by a vented flashback plug 28. In use, the chamber 26 in the needle hub 20 serves as a flashback chamber for the user to observe blood flashback, again in known manner.

A needle 30 is connected at its proximal end 32 to the distal end 22 of the needle hub 20. The needle 30 has a shaft 34 with a bore therethrough and having a sharpened needle tip 36 at its distal end. In the ready position, shown in FIGS. 1 and 2, the needle 30 extends through the internal chamber 12 of the catheter hub 4 and through the catheter 10, such that the sharpened needle tip 36 extends beyond the distal end of the catheter 10.

The needle 30 can be provided with a slot 38 in the distal end portion of the needle and spaced from the sharpened needle tip 36. In the ready position, the slot 38 lies within the catheter 10. In use, blood entering the bore in the needle shaft 34 flows out through the slot 38 and between the needle shaft 34 and the inner surface of the catheter 10 and provides a flashback indication to the user to indicate that the needle tip is properly located within a vein of the patient. Blood flowing through the bore in the needle shaft 34 enters the internal chamber 26 of the needle hub 20 and provides a primary flashback indication to the user, as mentioned above.

As noted above, the device 2 comprises a catheter hub 4 having an internal chamber 12. The catheter hub 4 has a proximal portion 40 and a distal portion 42. The internal chamber 12 is open at the proximal end 8 of the catheter hub 4 and extends through both the proximal and distal portions 40, 42 of the catheter hub 4, to communicate with the hollow catheter 10. The proximal portion 40 of the catheter hub 4 is generally conical in configuration and is formed with an internal taper 44, in particular a female Luer taper of standard form. The proximal portion 40 of the catheter hub 4 is provided with a protrusion 46 extending into the internal chamber 12 and located distally of the Luer taper. In the embodiment shown in FIGS. 1 and 2, the protrusion 46 is in the form of a circumferentially extending ring.

A valve opener 50 is disposed in the proximal portion 40 of the catheter hub 4. The valve opener 50 has an elongate stem 52 and a conical head 54 disposed at the distal end of the shaft 52. A bore extends longitudinally through the valve opener 50 and receives the shaft of the needle 30 in the ready position, as shown in FIGS. 1 and 2. The valve opener 50 is retained within the internal chamber 12 of the catheter hub 4 and its movement in the proximal direction is limited by the protrusion 46. The valve opener 50 is free to move in the distal direction under the action of a male fitting, such as a syringe, inserted into the proximal end 8 of the catheter hub 4.

The distal portion 42 of the catheter hub 4 has a generally flat profile, as shown in FIGS. 2 and 3, with wing members 60 extending from opposing sides of the catheter hub 4. The wing members 60 provide a means for securing the catheter hub 4 to the skin of a patient, for example by a suitable medical grade adhesive tape.

The proximal and distal portions 40, 42 of the catheter hub 4 may be formed as a single component or may be formed separately and thereafter joined together in the arrangement shown in FIGS. 1 to 3.

A flexible extension tube 62 extends from the distal portion 42 of the catheter hub 4. The distal end of the extension tube 62 opens into the internal chamber 12 of the catheter hub. The proximal end of the extension tube 62 is provided with a hollow connecting hub 64 having a proximal opening and provided with an internal taper, in particular a standard female Luer taper, for accepting a fitting, such as a syringe and the like, in known manner. A vented plug 66 may be provided at the proximal end of the connecting hub 64, as shown in FIG. 1, to maintain sterility. The connecting hub 64 may be used to introduce fluid into the extension tube 62 and the catheter assembly 2, for example by way of a syringe 68, shown in FIG. 3.

The distal portion 42 of the catheter hub 4 is further provided with a valve assembly 70 therein. The valve assembly 70 is disposed within the internal chamber 12 of the catheter hub and comprises a first valve portion 72, disposed in the internal chamber 12 distal of the valve opener 50, and a second valve portion 74. The second valve portion 74 being distal of the first valve portion 72.

The function of the first valve portion 72 is to seal the internal chamber 12 within the catheter hub 4, to prevent the flow of fluids in either the proximal or distal direction when the first valve portion is closed. The first valve portion 72 comprises a flexible valve disc 76 extending laterally across the internal chamber 12 of the catheter hub 4. The valve disc 76 is of a flexible, resilient material. The valve disc 76 is provided with one or more radial slits therein. In this way, the shaft 34 of the needle 30 extends through the valve disc 76 in the ready position, shown in FIGS. 1 and 2. Details of embodiments of the valve assembly are shown in FIGS. 7*a* to 7*c* and described hereinbelow.

With the needle in the ready position, the valve disc 76 closes around the outer surface of the needle shaft 34. With the needle 30 in the ready position, the slits are held open a sufficient distance to allow air to vent through the valve disc in the proximal direction, while being sufficiently closed so as to prevent the flow of blood through the valve disc in the proximal direction. By allowing air to vent through the valve disc 76 in this manner, the flow of blood from the slot 38 in the needle shaft 34 within the catheter 10 along the outside of the needle is possible, or without the slot 38 in the needle, as the needle tip is withdrawn into the hollow catheter tubing, thereby providing the secondary flashback.

The first valve portion 72 is a two-way valve. With the needle 30 retracted and the valve disc 76 closed, the flow of fluid in either the distal or the proximal direction within the catheter hub 4 is prevented. When there is no valve opener 50, then the valve disc 76 opens under the action of a reduced fluid pressure on the proximal side of the valve disc 76, for example by applying a vacuum to the proximal end of the catheter hub with a syringe engaged with the proximal end of the catheter hub 4. In this way, fluid may be withdrawn in the proximal direction through the catheter hub from the catheter 10 to the proximal end 8 of the catheter hub 4. Applying an increased fluid pressure to the proximal side of the disc valve 76, for example by way of a syringe engaged with the proximal end of the catheter hub 4, opens the valve and allows the passage of fluid in the distal direction through the catheter hub. In this way, fluid may be infused to the patient through the catheter hub 4 and catheter 10.

Engaging a fitting to the proximal end 8 of the catheter hub 4, such as a syringe or the like having a male taper, in particular a standard male Luer taper, urges the valve opener 50 in the distal direction. Movement of the valve opener 50 in the distal direction causes the head 54 of the valve opener to contact the valve disc 76 and open the slits in the disc. Fluid may be withdrawn from or infused to the patient with the valve open in this manner. The valve disc 76 is formed from a resilient material. As the male fitting is removed from engagement with the proximal end 8 of the catheter hub 4, the valve opener 50 is urged in the proximal direction by the valve disc 76 until the slits in the valve disc close. As noted above, further movement of the valve opener 50 in the proximal direction is prevented by the protrusion 46 in the proximal portion of the catheter hub 4.

The second valve portion 74 is disposed within the internal chamber 12 of the catheter hub 4 distal of the first valve portion 72. The function of the second valve portion 74 is to seal the opening in the distal end of the extension tube 62. The second valve portion 74 is in the form of a tube 80 of flexible, resilient material extending around the circumference of the internal chamber 12 of the catheter hub 4. The tube 80 conforms to the inner surface of the distal portion 42 of the catheter hub and provides a fluid-tight seal against the inner surface. The internal chamber 12 within the distal portion 42 of the catheter hub 4 may be generally cylindrical, in which case the tube 80 is generally cylindrical. Alternatively, the internal chamber 12 within the distal portion 42 of the catheter hub 4 may be elliptical in cross-section. The tube 80 for such an arrangement is also elliptical in cross-section. Embodiments of the valve assembly are shown in FIGS. 7a to 7c and described in more detail below.

As noted above, the tube 80 seals the distal end of the extension tube 62 at its opening into the internal chamber 12 in the catheter hub 4. An interference fit between the tube 80 and the catheter hub 4 urges the outer surface of tube 80 into contact with the inner surface of the distal portion 42 of the catheter hub, forming a fluid-tight seal. Increased fluid pressure within the extension tube 62 urges a portion of the tube 80 away from the inner surface of the internal chamber 12, allowing fluid to flow from the extension tube 62 into the internal chamber 12 and in a distal direction to the catheter 10. In this way, fluid may be introduced into the catheter 10 by way of the extension tube 62, for example from a syringe 68 connected to the connecting hub 64, as shown in FIG. 3.

In order to ensure a distally directed infusion towards the hollow catheter tubing, the proximal end of the tube 80 may be further stiffened by inserting a hard ring at the proximal end of the tube 80 just distal of the disc 76 or a flange can be extended from disc 76 that is held in a groove in the inside surface of the catheter hub. The hard ring is shown in dashed lines in FIG. 1, adjacent disc 76, and the groove of the catheter hub is shown as two spaced apart dashed line features in FIG. 1.

Figure 4:
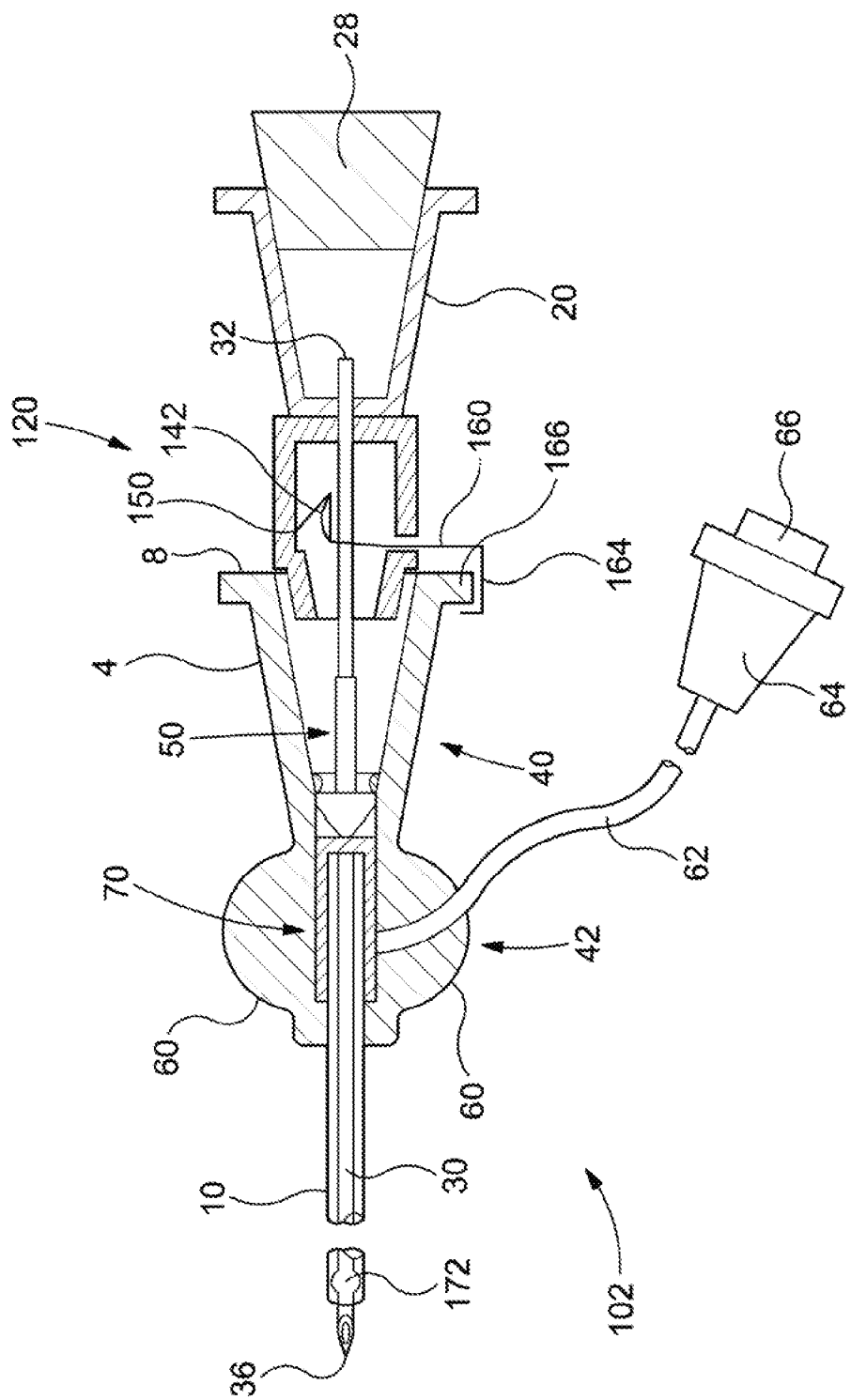
FIG. 4 is a cross-sectional view of a device according to a second embodiment of the present invention in a ready position.
Figure 5:
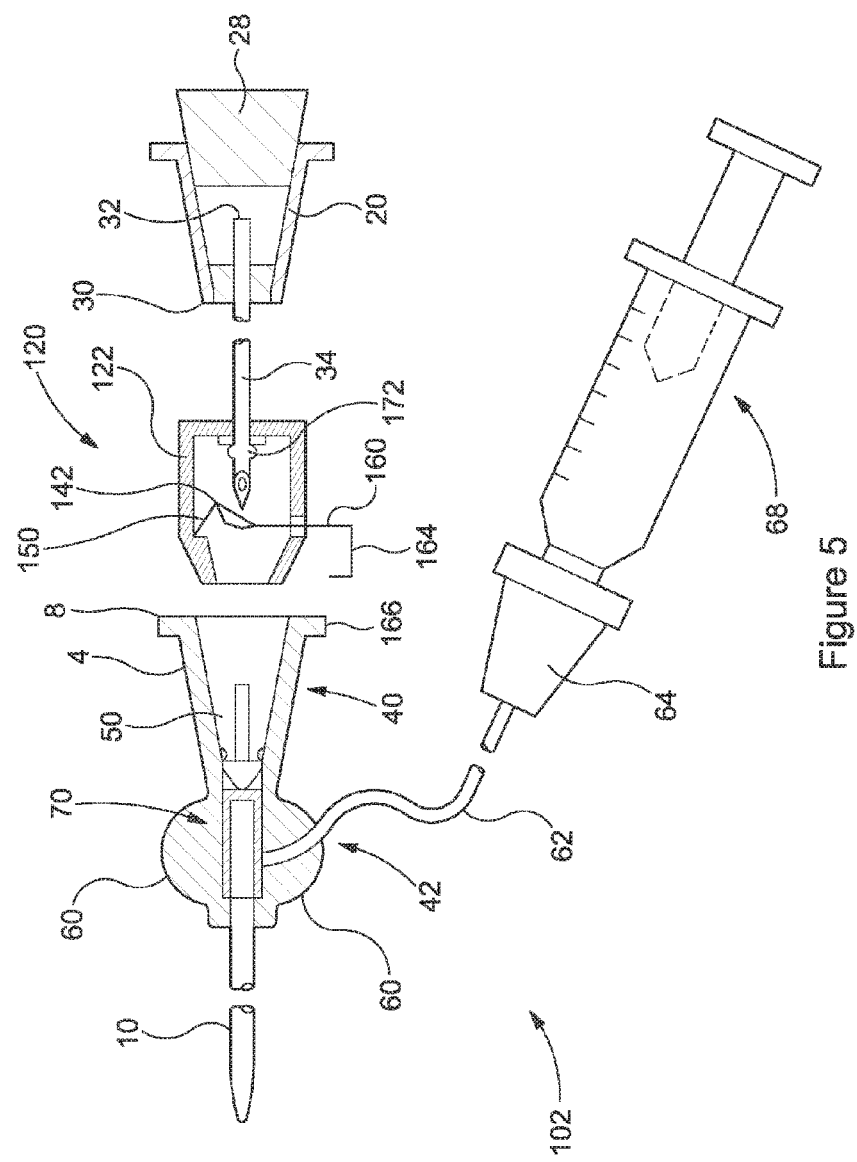
FIG. 5 is a cross-sectional view of the device of FIG. 4 in a protected position.

Turning to FIGS. 4 and 5, there is shown an alternative embodiment of the device of the present invention. The device of this embodiment, generally indicated as 102, comprises a catheter hub, catheter, needle hub and needle, valve assembly and valve opener, and extension tube of the same general configuration as the embodiment of FIGS. 1 and 2 and described above. Features of the embodiment of FIGS. 4 and 5 common to the embodiment of FIGS. 1 and 2 are indicated using the same reference numerals.

The embodiment of FIGS. 4 and 5 comprises a needle guard assembly disposed between the distal end of the needle hub 20 and the proximal end of the catheter hub 4, when the device is in the ready position, as shown in FIG. 4. The needle guard assembly, generally indicated as 120, is shown in the ready position in greater detail in FIG. 4a.

There can be some overlapping of the proximal end of the needle guard and the distal end of the needle hub and/or overlapping of the distal end of the needle guard and the proximal end of the catheter hub.

Figure 4A:
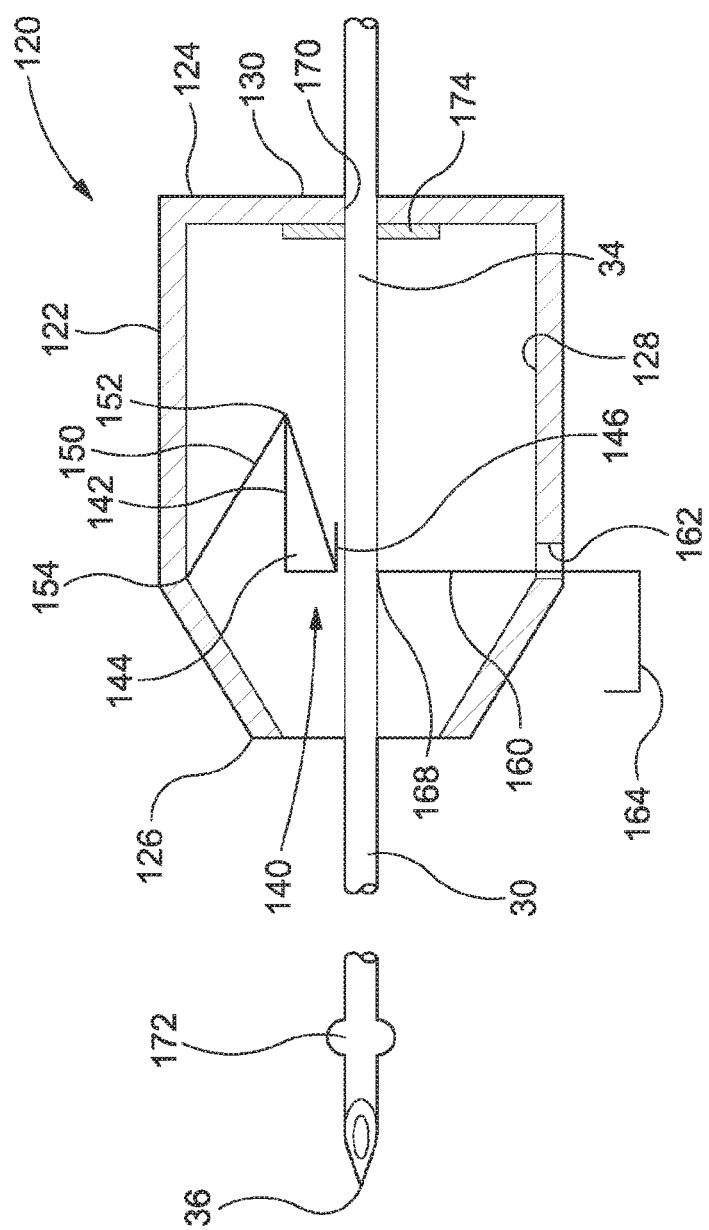
FIG. 4a is an enlarged cross-sectional view of the needle guard assembly of the device of FIG. 4.

Referring to FIG. 4a, the needle guard assembly 120 comprises a generally cylindrical needle guard housing 122 having a proximal end 124 and a distal end 126. Alternative shapes for the needle guard housing include a generally rectangular cross-section. The distal end portion is conical in form and provided with a standard taper, in particular a standard male Luer taper. In the ready position shown in FIG. 3, the conical distal end 126 of the needle guard housing 122 extends within the female Luer taper in the proximal end 8 of the catheter hub 4.

The needle guard housing 122 comprises an internal chamber 128 open at the distal end 126 and closed at the proximal end 124 by a proximal wall 130. In the ready position, the needle shaft 34 extends through the internal chamber 128 of the needle guard housing 122 and the proximal wall 130, as shown in FIGS. 4 and 4a.

A needle guard 140 is disposed within the needle guard housing 122 and comprises a needle trap 142 having lateral or side members 144 extending proximally from the needle trap 142. The needle trap further comprises a retaining member 146. When the needle 30 is retracted to the protected position shown in FIG. 5, the side members 144 and retaining member 146 prevent the needle trap 142 moving laterally relative to the needle and exposing the needle tip.

The needle guard 140 further comprises a resilient arm 150 pivotally connected at a first end 152 to the needle trap 142 and bearing on the inner surface of the needle guard housing 122 at a second end 154.

The needle guard 140 further comprises a coupling arm 160 pivotally connected at a first end to the needle trap 142 at a position opposite to the connection between the needle trap and the resilient arm 150. The coupling arm 160 extends from the needle trap 142 across the internal chamber 128 and through an opening 162 in the needle guard housing 122. The coupling arm 160 is provided with a hook 164 at its free end outside the needle guard housing 122, which engages with a flange 166 on the exterior of the proximal end 8 of the catheter hub 4, as shown in FIG. 4. An opening 168 is provided in the coupling arm 160, through which the needle shaft 34 extends in the ready position, as shown in FIG. 4a.

In the ready position shown in FIGS. 4 and 4a, the needle trap 142 is held to one side of the needle shaft 34 in a folded position overlying the resilient arm 150. The coupling arm 160 is held by the needle shaft 34 retracted within the needle guard housing 122, in turn holding the hook 164 engaged with the flange 166 on the proximal end 8 of the catheter hub 4.

The needle guard 140 is inherently resilient urging the needle guard into a straight orientation. In the ready position the needle shaft 34 holds the needle trap 142 against the inherent bias of the needle guard. When the needle 30 is retracted to the protected position shown in FIGS. 5 and 5a, in particular, when the needle tip 36 is moved to a position within the needle guard housing 122 proximal of the needle trap and the coupling arm, the resilience of the needle guard 140 urges the needle trap 142 into the blocking position across the needle tip 36. The same movement urges the hook 164 of the coupling arm out of engagement with the proximal end 8 of the catheter hub 4, thereby releasing the needle guard assembly 120 from the catheter hub. The retaining member 146 is positioned to engage with the needle shaft at the sharpened needle tip 36 to prevent the coupling arm being pushed in the reverse direction in the needle guard housing and realigning the opening 168 in the coupling arm with the needle tip 36.

Figure 5A:
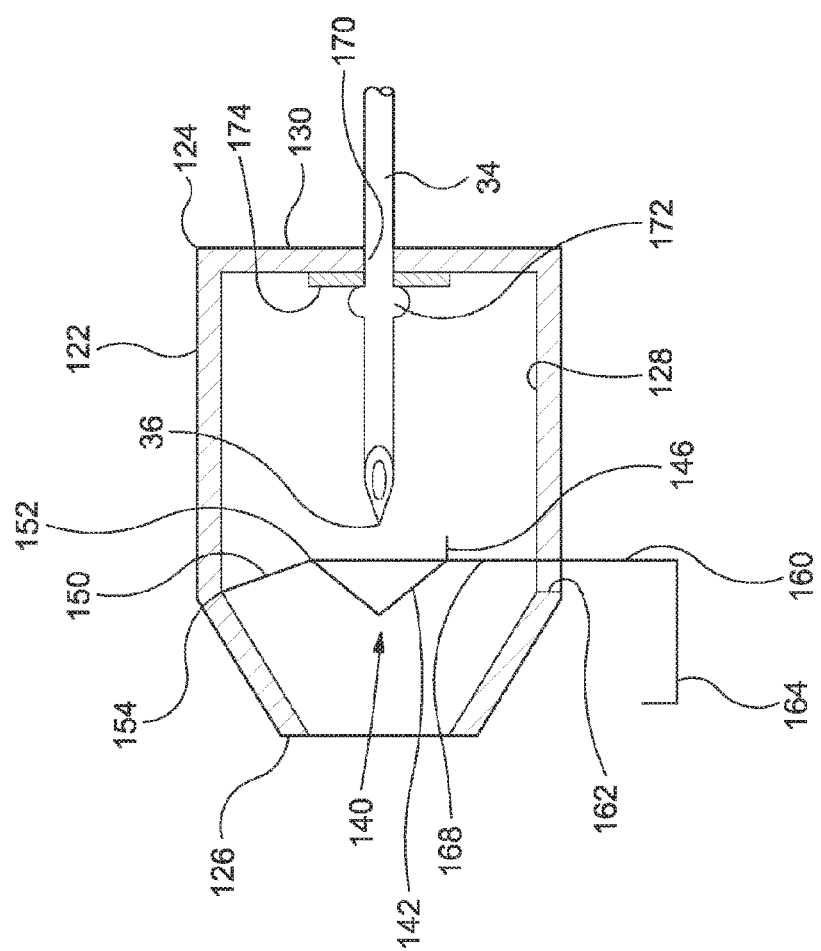
FIG. 5a is an enlarged cross-sectional view of the needle guard assembly of the device of FIG. 5.

As shown in the figures, the needle shaft 34 extends through an opening 170 in the proximal wall 130 of the needle guard housing 122. The needle 30 is provided with a bulge, in the form of a crimp 172, in the distal end portion of the needle shaft spaced from the needle tip 36. In the ready position, the crimp 172 is located within the catheter 10. The crimp 172 has a diameter greater than the radial dimension of the opening 170 in the proximal wall 130 of the needle guard housing 122. In the protected position shown in FIGS. 5 and 5a, the needle tip 36 is within the needle guard housing 122. The needle 30 is prevented from moving distally relative to the needle guard assembly 120 by the needle trap 142. Further proximal movement of the needle 30 relative to the needle guard assembly 120 is prevented by the crimp 172 engaging with the proximal wall 130, as shown in FIG. 5a. A metal washer 174 may be provided on the inner surface of the proximal wall 130, to engage with the crimp and prevent the crimp 172 being inadvertently pulled through the proximal wall. This allows the needle guard housing 122 to be formed from a relatively soft material, such as moulded from plastic.

Figure 6:
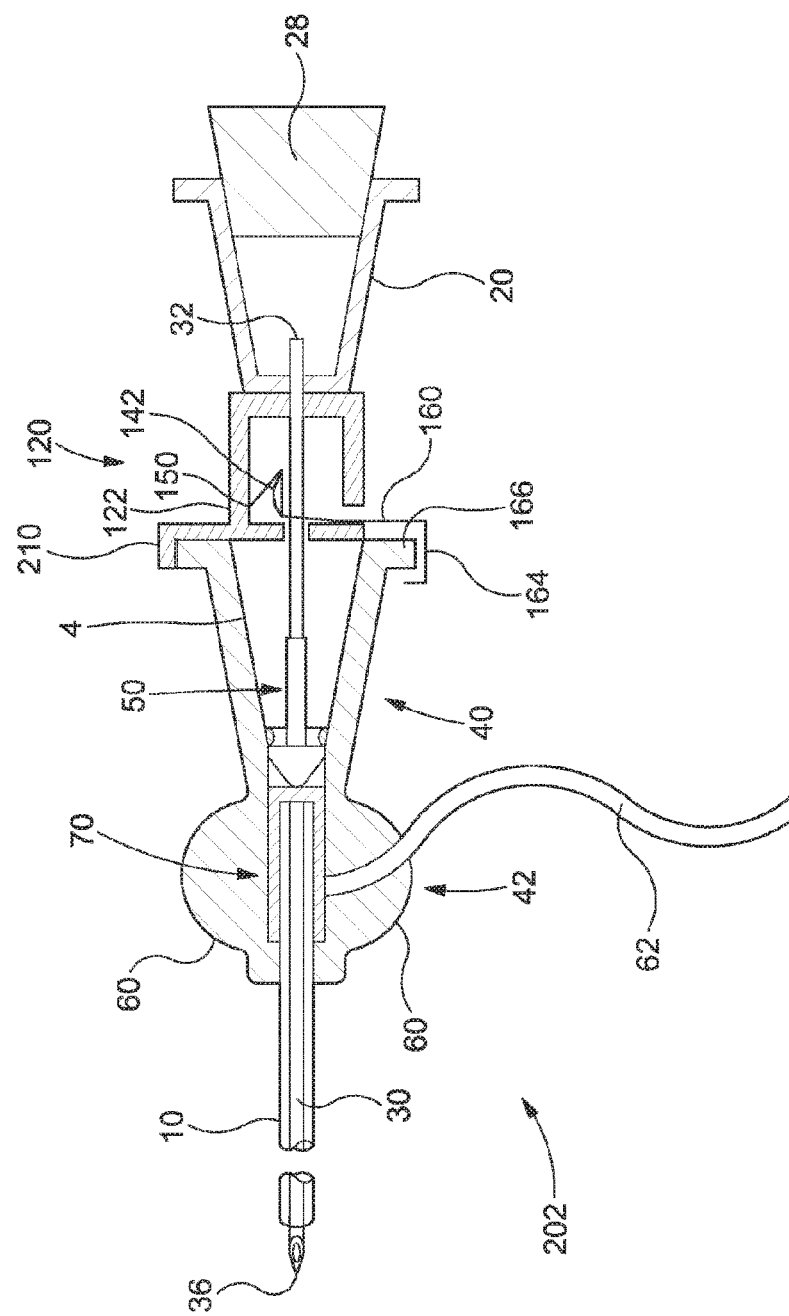
FIG. 6 is a cross-sectional view of a device according to a third embodiment of the present invention in a ready position.

Turning to FIG. 6, there is shown an alternative embodiment of the device of the present invention. The device of this embodiment, generally indicated as 202, comprises a catheter hub, catheter, needle hub and needle, valve assembly and valve opener, and extension tube of the same general configuration as the embodiment of FIGS. 1 and 2 and described above. Features of the embodiment of FIG. 6 common to the embodiment of FIGS. 1 and 2 are indicated using the same reference numerals. The embodiment of FIG. 6 also comprises a needle guard assembly having a needle guard of the same general configuration as that of the embodiment of FIGS. 4 and 5. Features of the embodiment of FIG. 6 common to the embodiment of FIGS. 4 and 5 are indicated using the same reference numerals.

The device is shown in the ready position in FIG. 6. In the needle guard assembly 120 of FIG. 6, the needle guard housing 122 is located wholly outside the catheter hub 4. The needle guard assembly 120 is coupled to one side of the flange 166 of the proximal end of the catheter hub 4 as in FIG. 4 and described above. To stabilise the needle guard housing 122 on the proximal end of the catheter hub 4, the needle guard housing is provided with an exterior distal arm 210 extending from the distal end 126 of the housing on the opposite side to the coupling arm 160. The exterior distal arm 210 engages with the exterior flange 166 at the proximal end of the catheter hub on the opposite side of the catheter hub to the engagement of the coupling arm 160.

As the needle is retracted to the protected position, the coupling arm 160 and its hook 164 are released from the flange 166 of the catheter hub 4. The exterior distal arm 210 is thereby released from engagement with the flange 166 and the needle guard assembly 120, with the blocked needle tip 36 therein, may be removed from the catheter hub 4.

Figure 7:
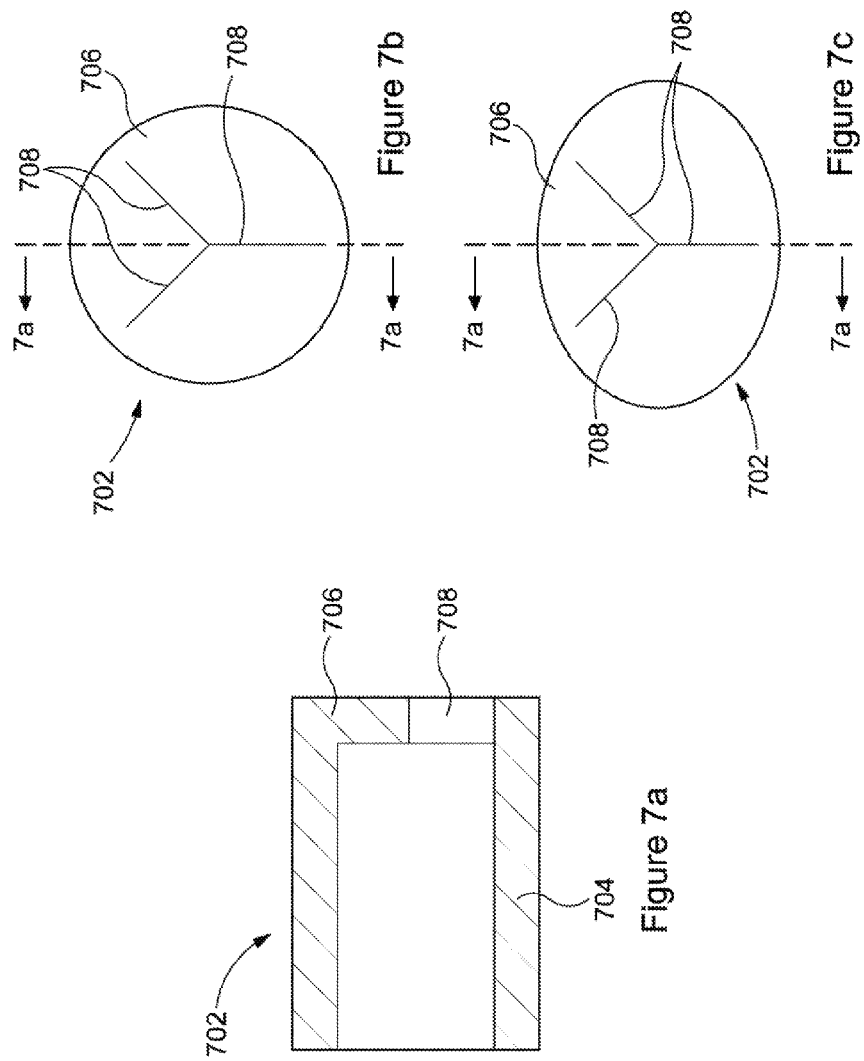

Turning to FIG. 7, embodiments of the valve assembly for use in the distal portion 42 of the catheter hub 4 will now be described.

Referring to FIG. 7a, there is shown a longitudinal cross-sectional view of a valve assembly for use in the catheter assembly of the present invention. The valve assembly, generally indicated as 702, is formed from a flexible material impermeable to the passage of liquid and gas. The valve assembly 702 comprises a generally tubular second valve portion 704 and a first valve portion in the form of a valve disc 706 at the proximal end of the second valve portion.

Views of the valve disc 706 of embodiments of the valve assembly 702 are shown in FIGS. 7b and 7c. The valve assembly 702 may have a generally circular cross-section, as shown in FIG. 7b. Alternatively, the valve assembly 702 may be generally flattened and have an elliptical cross-section, as shown in FIG. 7c. The portion of the internal chamber 12 within the distal portion 42 of the catheter hub 4 will conform in shape to the valve assembly 702, such that the valve assembly is a tight fit within the chamber and the second valve portion 704 is in close contact with the inner surface of the chamber, so as to provide a fluid tight seal between the valve assembly and the inner surface of the catheter hub.

The valve disc 706 is provided with a plurality of slits 708 therein. The embodiments shown in FIGS. 7b and 7c each have an array of three slits extending radially outwards from the centre of the valve disc 706. Other arrangements of the slits 708 in the valve disc 706 are possible, for example a single slit.

In the ready position, the shaft 34 of the needle extends through the valve disc 706. The shaft of the needle holds the slits 708 open sufficient to allow gas to pass through the valve disc, in particular in the proximal direction, but insufficient to allow blood to pass through the valve disc. In this way, the user may be provided with a flashback indication, as described above.

As described above, the valve disc 706 is resilient. In particular, the valve opener 50 moves in the distal direction against the resilient bias of the valve disc, when acted upon by a male fitting inserted into the proximal end 8 of the catheter hub 4. Upon removal of the fitting, the valve disc urges the valve opener in the proximal direction, allowing the valve disc to close and seal the internal chamber of the catheter hub.

Figure 8:
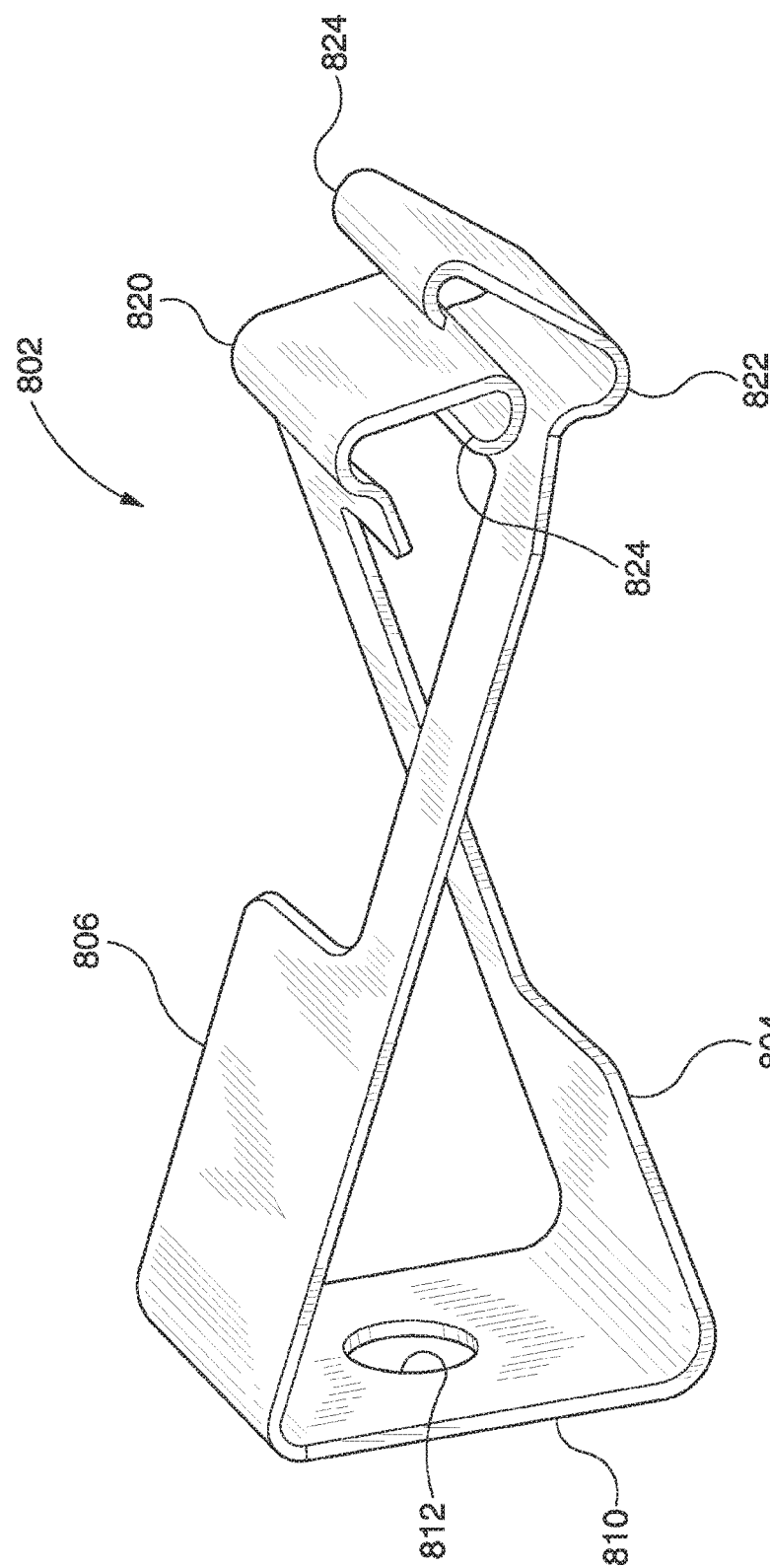
FIG. 8 is a perspective view of one embodiment of needle guard for use in the catheter assembly of the present invention.

As noted above, the needle guard may be of an arrangement that is retained within the catheter hub in the ready position. One preferred embodiment of such a needle guard is shown in FIG. 8. The needle guard is in the form of a needle clip, generally indicated as 802, which is made of a resilient material, such as metal, having arms 804, 806 extending in a distal direction from opposite sides of a proximal wall 810. The proximal wall 810 has a hole 812 for the passage of the needle. The needle shaft is provided with a bulge, for example in the form of a crimp, proximal of the tip of the needle as described hereinbefore and shown in the figures. The diameter of the hole 812 in the proximal wall 810 of the needle clip 802 is smaller than the maximum transverse dimension of the needle at the bulge, so that the needle clip 802 is held in the protected position on the needle tip by means of the bulge.

In the embodiment shown in FIG. 8, the arms 804, 806 intersect and extend on both sides of the needle and each has at its distal end an end portion 820, 822 which is widened to approximately the width of the proximal wall 810 and which, in the ready position, lies with elastic pretensioning on the outer circumference of the needle. Alternatively the arms do not have to cross and can extend along opposing sides of the needle shaft. Upon reaching the needle tip, the distal end portions 820, 822 are moved by spring action into the protected position in which the two widened end portions 820, 822 engage over and block the needle tip. For this purpose, the distal ends 820, 822 of the arms 804, 806 are slightly offset with respect to one another in the longitudinal direction or the arms 804, 806 are of different lengths, so that it is thus ensured that the two distal end portions 820, 822 of the arms engage over the needle tip. Alternatively only the longer arm 806 can have an end portion 822 to block the needle tip. Preferably, the longer arm 806 has an endmost portion 824 curved inward at the free edge, in order to ensure that the needle tip is covered even if an attempt is made to push the needle clip 802 back from the protected position on the needle, the inwardly curved end portion 824 hooking onto the needle tip. The needle clip 802 as a whole can be made very compact and only about 7 mm long, for example.

The invention claimed is:

1. A catheter assembly comprising:
    a catheter hub having a chamber therein, the catheter hub having a distal end and a proximal end, the catheter hub being connectable at the proximal end of the catheter hub to a device for infusion or withdrawal of fluids to or from the chamber within the catheter hub;
    a hollow tubular catheter having a proximal end and a distal end, the catheter being connected at the proximal end of the catheter to the distal end of the catheter hub, an interior of the catheter in fluid communication with the chamber of the catheter hub;
    a needle having a sharpened needle tip, the needle extending through the chamber in the catheter hub and the catheter with the needle tip extending beyond the distal end of the catheter in a ready position;

a hollow extension tube having a distal end and a proximal end, the extension tube being connected at the distal end of the extension tube to the catheter hub between the proximal and distal ends of the catheter hub, an opening at the distal end of the extension tube opening into the chamber within the catheter hub, the extension tube connectable at the proximal end of the extension tube to a device for infusing fluid through a passage into the chamber within the catheter hub;

a valve assembly disposed within the chamber of the catheter hub, the valve assembly comprising:

a first valve member preventing a flow of fluid through the chamber to or from the proximal end of the catheter hub, the second valve member being a two-way valve and openable to permit the flow of fluid through the chamber in the catheter hub in both a proximal and a distal direction; a second valve member being resilient and flexible for moving between closing and opening positions, the first valve member closing the distal end of the extension tube to close fluid flow through the passage of the extension tube and openable under an action of a pressurized fluid within the extension tube to permit fluid flow through the passage of the extension tube; and a needle guard assembly slidably mounted on the needle to cover the needle tip.

2. The catheter assembly according to claim 1, wherein a distal hub portion of the catheter hub is generally flattened.

3. The catheter assembly according to claim 2, wherein the extension tube opens into the distal hub portion of the catheter hub.

4. The catheter assembly according to claim 1, wherein the needle comprises an opening in a shaft of the needle in a distal end portion of the needle.

5. The catheter assembly according to claim 4, wherein the opening is disposed within the catheter in the ready position.

6. The catheter assembly according to claim 1, wherein the second valve member is a one-way valve between the extension tube and the chamber of the catheter hub.

7. The catheter assembly according to claim 1, wherein the first valve member is between the extension tube and the chamber of the catheter hub.

8. The catheter assembly according to claim 7, wherein the second valve member is aligned with the opening of the extension tube.

9. The catheter assembly according to claim 1, wherein the second valve member comprises a resilient valve body.

10. The catheter assembly according to claim 9, wherein the valve body is a tubular body.

11. The catheter assembly according to claim 10, wherein the tubular body is disposed within the chamber of the catheter hub in contact with an inner surface of a wall of the catheter hub.

12. The catheter assembly according to claim 11, wherein the second valve member is openable by a portion of the tubular body urged away from the inner surface of the wall of the catheter hub.

13. The catheter assembly according to claim 1, wherein the first valve member comprises a resilient valve disc extending laterally across the chamber of the catheter hub.

14. The catheter assembly according to claim 13, wherein the disc is provided with one or more slits therein.

15. The catheter assembly according to claim 1, wherein the first valve member forms a seal around a shaft of the needle in the ready position.

16. The catheter assembly according to claim 1, further comprising a valve opener disposed within the chamber in the catheter hub proximally of the valve assembly.

17. The catheter assembly according to claim 16, wherein the valve opener has a passage therethrough or therearound for a passage of fluid.

18. The catheter assembly according to claim 1, wherein the needle guard assembly is disposed wholly or partly within the chamber of the catheter hub.

19. The catheter assembly according to claim 18, wherein the needle guard assembly is releasably engaged with the catheter hub, such that the needle has a protected position in which the needle tip is blocked by the needle guard assembly as the needle guard assembly is released from the catheter hub.

20. The catheter assembly according to claim 1, wherein the needle guard assembly is disposed outside the catheter hub.

21. The catheter assembly according to claim 1, wherein the needle guard assembly is releasably engaged with the catheter hub in the ready position.

22. The catheter assembly according to claim 21, in which movement of the needle to a protected position releases the needle guard assembly from engagement with the catheter hub.

23. The catheter assembly according to claim 1, wherein the needle guard assembly comprises a needle guard housing.

24. The catheter assembly according to claim 1, wherein first and second arms of the needle guard assembly extend in a distal direction from a proximal wall.

25. The catheter assembly according to claim 1, further comprising means for limiting movement of the needle in a proximal direction relative to the needle guard assembly.

26. The catheter assembly according to claim 25, wherein the limiting means comprises a bulge in a distal end portion of a needle shaft.

27. The catheter assembly according to claim 26, wherein the bulge is non-circular.

28. The catheter assembly according to claim 26, wherein the needle guard assembly comprises a proximal wall having an opening therein, the needle shaft extending through the opening in the proximal wall, the bulge having a radial dimension that is greater than a diameter dimension of the opening in the proximal wall.

29. The catheter assembly according to claim 26, wherein the bulge lies within the catheter in the ready position.

30. The catheter assembly according to claim 1, wherein first and second arms of the needle guard assembly intersect.

31. The catheter assembly according to claim 1, wherein at least one of first and second arms of the needle guard assembly comprises a distal end portion for blocking the needle tip.

32. The catheter assembly according to claim 31, wherein the distal end portion is formed with the first arm, and wherein the second arm has a distal end portion, and wherein the distal end portions of the first arm and the second arm are slightly offset with respect to one another.

33. The catheter assembly according to claim 31, wherein the first and second arms are of different lengths.

34. The catheter assembly according to claim 33, wherein the longer of the first and second arms has an endmost portion curved inwardly at a free edge.

35. The catheter assembly according to claim 1, wherein the second valve member is openable by a fluid pressure within the extension tube.

36. A catheter assembly comprising:

a catheter hub having a chamber therein, the catheter hub having a distal end and a proximal end, the catheter hub being connectable at the proximal end of the catheter hub to a device for infusion or withdrawal of fluids to or from the chamber within the catheter hub;

a hollow tubular catheter having a proximal end and a distal end, the catheter being connected at the proximal end of the catheter to the distal end of the catheter hub, an interior of the catheter opening into the chamber within the catheter hub;

a needle having a sharpened needle tip, the needle extending through the chamber of the catheter hub and the catheter with the needle tip extending beyond the distal end of the catheter in a ready position;

a hollow extension tube having a distal end and a proximal end, the extension tube being connected at the distal end of the extension tube to the catheter hub between the proximal and distal ends of the catheter hub, the extension tube opening at the distal end of the extension tube into the chamber within the catheter hub, the extension tube connectable at the proximal end of the extension tube to a device for infusing fluid through a passage into the chamber within the catheter hub;

a valve assembly disposed within the chamber of the catheter hub, the valve assembly being formed from a flexible material and comprising:

a unitarily formed valve body comprising a first valve portion for blocking fluid flow through the proximal end of the catheter hub and a second valve portion located distally of the first valve portion for blocking fluid flow into the distal end of the hollow extension;

the first valve portion forming a first seal and comprising slits to permit flow through the chamber of the catheter hub in both a proximal direction and a distal direction when the slits are opened; and the second valve portion forming a second seal at the distal end of the extension tube comprising a valve body in a form of a tube of flexible resilient material extending around a circumference of the chamber to prevent flow between the extension tube and the chamber; and a needle guard slidably mounted on the needle to cover the needle tip.

37. The catheter assembly according to claim 36, wherein the tube of the second valve portion conforms to an inner surface of the chamber to form the second seal.

38. The catheter assembly according to claim 36, wherein the second valve portion has a proximal end and a distal end, and a rigid ring is disposed at the proximal end of the second valve portion.

39. The catheter assembly according to claim 36, wherein the catheter hub defines a holding groove inside an inner surface of the chamber of the catheter hub, and the first valve portion comprises a body and a flange extending from the body, the flange of the first valve portion being held in the holding groove.

40. The catheter assembly according to claim 36, further comprising a valve actuator for opening the first valve portion.

* * * * *

UNITED STATES PATENT AND TRADEMARK OFFICE
CERTIFICATE OF CORRECTION

PATENT NO. : 10,004,891 B2
APPLICATION NO. : 15/042031
DATED : June 26, 2018
INVENTOR(S) : Kevin Woehr Page 1 of 2

It is certified that error appears in the above-identified patent and that said Letters Patent is hereby corrected as shown below:

On the Title Page

In Column 1, item (*) Notice, Line 3, after "0 days." delete "days.".

On page 2, Column 1, item (30) Foreign Application Priority Data, Line 3, delete "2013 1 052778" and insert -- 2013 1 052778.3 --, therefor.

In the Specification

In Column 11, Line 58, delete "first" and insert -- second --, therefor.

In Column 11, Line 60, after "and a" delete "second" and insert -- first --, therefor.

In Column 11, Line 60, after "The" delete "second" and insert -- first --, therefor.

In Column 11, Line 61, delete "first" and insert -- second --, therefor.

In Column 11, Line 62, delete "first" and insert -- second --, therefor.

In Column 11, Line 65, before "valve portion is closed" delete "first" and insert -- second --, therefor.

In Column 11, Line 65, before "valve portion 72" delete "first" and insert -- second --, therefor.

In Column 12, Line 20, delete "first" and insert -- second --, therefor.

In Column 12, Line 53, delete "second" and insert -- first --, therefor.

In Column 12, Line 54, delete "first" and insert -- second --, therefor.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,004,891 B2

In Column 12, Line 55, delete "second" and insert -- first --, therefor.

In Column 12, Line 57, delete "second" and insert -- first --, therefor.